United States Patent [19]

Mitchell, III et al.

[11] 4,408,058

[45] Oct. 4, 1983

[54] PREPARATION OF ORTHO-SULFOBENZOIC ACID ANHYDRIDE BY CATALYZED THERMOLYSIS

[75] Inventors: Mark L. Mitchell, III; Richard P. Carr, both of Cincinnati, Ohio

[73] Assignee: The Sherwin-Williams Company, Cleveland, Ohio

[21] Appl. No.: 382,316

[22] Filed: May 26, 1982

[51] Int. Cl.³ .................................... C07D 327/04
[52] U.S. Cl. ........................................... 549/33
[58] Field of Search .................................. 549/33

[56] References Cited

U.S. PATENT DOCUMENTS 4,042,600  7/1977  DiPippo .......................... 260/327
4,259,499  3/1981  DiPippo .......................... 548/211

OTHER PUBLICATIONS

*Friedel-Crafts and Related Reactions*, vol. 3, G. Olah, pp. 1319–1347.

*Primary Examiner*—Richard Raymond
*Attorney, Agent, or Firm*—Robert E. McDonald; James V. Tura

[57] ABSTRACT

This invention relates to a process for the synthesis of ortho-sulfobenzoic acid anhydride which comprises heating a 2-sulfohalide benzoate in the presence of a catalytic amount of a Friedel-Crafts catalyst. Especially preferred in the practice of this invention is the reaction of ortho-carbomethoxybenzenesulfonyl chloride in the presence of a zinc or iron halide to produce ortho-sulfobenzoic acid anhydride.

25 Claims, No Drawings

PREPARATION OF ORTHO-SULFOBENZOIC ACID ANHYDRIDE BY CATALYZED THERMOLYSIS

BACKGROUND OF THE INVENTION

1. Field of the Invention

This invention relates to a process for the synthesis of ortho-sulfobenzoic acid anhydride which comprises heating a 2-sulfohalide benzoate in the presence of a catalytic amount of a Friedel-Crafts catalyst.

Ortho-sulfobenzoic acid anhydride is a useful chemical intermediate in the manufacture of dyes, saccharin, and sulfonephthalein dyes and indicators. It is also useful as a polymerization inhibitor.

2. Description of the Prior Art

Several methods for the synthesis of ortho-sulfobenzoic acid anhydride have been described in the prior art. For example, U.S. Pat. Nos. 4,042,600 and 4,259,499 teach the preparation of ortho-sulfobenzoic acid anhydride by the pyrolysis of 2-sulfohalide benzoates. These disclosures, however, do not indicate the use of catalysts of any kind, and the procedure taught in these patents does not give high yields at reasonable processing temperatures.

H. T. Clark and E. E. Dreger, Org. Syn. Coll. Vol. I, Second Edition, page 495 (1941), teach the synthesis of ortho-sulfobenzoic acid anhydride by the reaction of acid ammonium ortho-sulfobenzoate with excess thionyl chloride, usually in an aromatic solvent. This reaction does not proceed in high yield, and has the additional disadvantage that sulfur dioxide and hydrochloric acid gas are given off in the course of the reaction.

Belgian Patent No. 629,100 teaches the ring-closure reaction of ortho-sulfobenzoic acid.

SUMMARY OF THE INVENTION

This invention relates to a novel synthesis of ortho-sulfobenzoic acid anhydride by heating 2-sulfohalide benzoates in the presence of a catalytic amount of a Friedel-Crafts catalyst at effective temperatures to produce excellent yields of the anhydride.

The process taught herein can be run neat, or it may be run in the presence of a solvent which is essentially inert to the conditions of the reaction. The effective temperature range for heating the 2-sulfohalide benzoates is at least enough to melt the 2-sulfohalide benzoate and preferably should range from about 130° C. to 400° C. Especially preferred in the practice of this invention is a temperature range of about 150° C. to 250° C.

It is therefore an object of this invention to provide a novel process for the synthesis of ortho-sulfobenzoic acid anhydride. It is a further object of this invention to utilize Friedel-Crafts catalysts to promote the catalytic thermal conversion of 2-sulfohalide benzoates to ortho-sulfobenzoic acid anhydride. A more limited object of this invention is to provide a process for the synthesis of ortho-sulfobenzoic acid anhydride which comprises heating ortho-carbomethoxybenzenesulfonyl chloride in the presence of a catalytic amount of a Friedel-Crafts catalyst. These and other objects of this invention will be apparent from the following description.

DETAILED DESCRIPTION OF THE INVENTION

The reaction of this invention is shown below (representatively using ortho-carbomethoxybenzenesulfonyl chloride and zinc chloride catalyst)

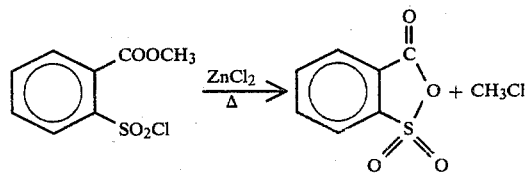

This reaction produces not only the anhydride product but also produces methyl chloride in excellent yield. Replacing the methyl group with other aliphatic, aryl or aralkyl groups will yield the corresponding aliphatic, aryl or aralkyl halide as a co-product with the anhydride.

The process of this invention typically involves 2-sulfohalide benzoates having the structure:

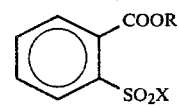

wherein R is aliphatic of 1 to about 14 carbons; aryl of 6 to about 20 carbons; or aralkyl of 7 to about 20 carbons and X is Cl or Br. R can be saturated or unsaturated and could be straight chain, branched, or cyclic. Preferably R is alkyl of 1 to about 5 carbons.

Representative examples of these 2-sulfohalide benzoates include: ortho-carbomethoxybenzenesulfonyl chloride, ortho-carbomethoxybenzenesulfonyl bromide, ortho-carboisobutoxybenzenesulfonyl chloride, ortho-carboethoxybenzenesulfonyl chloride and so forth.

The Friedel-Crafts catalysts generally useful in the practice of this invention are those Lewis acid catalysts capable of abstracting a halide atom in a Friedel-Crafts alkylation, acylation or sulfonylation. Preferred are the metal containing Lewis acid catalysts, especially the metal halides. The Friedel-Crafts metal halide catalysts are covalent compounds having an electrondeficient central metal atom capable of electron acceptance from electron-rich reagents. Normally the halide atom is chlorine or bromine.

Metal halides having Friedel-Crafts catalytic activity include Group IB halides such as cuprous chloride and auric chloride; Group IIA halides such as berylium chloride; Group IIB halides such as zinc chloride; Group IIIA halides such as aluminum bromide and aluminum chloride; Group IIIB halides such as gallium chloride and indium chloride; Group IVB halides such as stannic chloride; Group IVA halides such as titanium tetrachloride; Group VB halides such as antimony pentafluoride; Group VIA halides such as molybdenum pentachloride; and Group VIII halides such as ferric chloride and ferrous chloride. Preferred metal halides are the halides of antimony, molybdenum, iron, boron, tin, zinc and titanium. Ferric chloride and zinc chloride have shown special utility. Aluminum chloride provides good yields of the alkyl halide co-product but apparently forms an aluminum complex with the anhydride which makes recovery of the pure anhydride more difficult. Therefore, although the aluminum halides do work, they are not the preferred catalysts.

Catalytic amounts of the catalysts will typically range from about 0.01% by weight of the 2-sulfohalide benzoate. Especially preferred is a level of catalyst ranging between about 0.1 to about 3.0% by weight of the 2-sulfohalide benzoate.

The process of this reaction can be conveniently conducted either with or without an inert solvent. When the 2-sulfohalide benzoate is heated in the presence of a solvent, it is generally preferred to use a solvent having a boiling point of at least about 130° C. Use of a solvent having a boiling point of at least about 150° C. is especially preferred. Generally preferred in the practice of this invention is the use of aromatic solvents having electron withdrawing groups on the aromatic ring. Representative examples include chlorobenzene, dichlorobenzene, benzonitrile and the like. If the reaction is not run under increased pressure, higher boiling solvents will provide higher reaction temperatures and higher yields in shorter reaction times.

The following examples are intended to illustrate the invention but are not presented as limitations upon the scope of the claims. Unless otherwise indicated, the term "parts" means parts by weight.

EXAMPLE 1

A reaction vessel equipped with a Claisen adapter, which in turn is fitted with a nitrogen inlet tube extending below the level of the reaction mixture and an adaptor with flexible tubing extending to a cold trap, was charged with 63 parts of orthocarbomethoxybenzenesulfonyl chloride (commercially available from The Sherwin-Williams Company), and 0.63 parts of zinc chloride (technical grade, available from the J. T. Baker Chemical Company).

The reactants were heated to about 150° C. with agitation and maintained at that temperature for about two hours while a slight nitrogen purge was maintained to preclude moisture. At the end of this period, a quantity of methyl chloride (approximately 95% of the theoretical yield) was observed in the cold trap.

One hundred seventy-five parts by weight of toluene were added to the reactant mixture; and the resultant mixture was filtered hot to remove the catalyst and a small amount of sludge. Upon cooling, a white crystalline product precipitated from the toluene solution, and the product was separated by vacuum filtration and dried in a vacuum oven at 100° C. The white crystalline product was approximately 43.0 parts of ortho-sulfobenzoic acid anhydride having a melting point of 126°–128° C., and having infrared bands at 1820 cm$^{-1}$ and 1840cm$^{-1}$ indicating an anhydride structure. This yield represents approximately 87% of the theoretical yield.

EXAMPLE 2

The procedure of Example 1 was repeated except the catalyst and the ortho-carbomethoxybenzenesulfonyl chloride were heated to 200° C. instead of 150° C. and maintained at that temperature for one hour. This procedure provided a yield of approximately 91% of the theoretical amount of ortho-sulfobenzoic acid anhydride.

EXAMPLE 3

The apparatus of Example 1 was modified by placing a Friedrichs condenser between the reaction vessel and the adapter. The vessel was charged with a solution of 47 parts ortho-carbomethoxybenzenesulfonyl chloride in 125 parts ortho-dichlorobenzene and 0.4 parts zinc chloride. The solution was heated at reflux (approximately 170° C.) overnight (approximately 20 hours). At the end of that period approximately 8.2 parts (80% of theoretical) of methyl chloride was in the cold trap. The reaction mixture was filtered to remove the catalyst and then allowed to cool yielding 32.8 parts (89% of theoretical) of solid o-sulfobenzoic acid anhydride having a melting point of 126°–129° C. having infrared bands at 1820 cm$^{-1}$ and 1840 cm$^{-1}$ showing the anhydride structure.

EXAMPLE 4

Similar results to that obtained in Example 3 can be obtained in an experiment replacing the zinc chloride with the same amount of ferric chloride and by replacing the dichlorobenzene with xylene.

COMPARATIVE EXAMPLE A

By way of comparison, the procedure of Example 1 was repeated except the zinc chloride was eliminated. After sixteen hours at 150° C. no anhydride band was visible in the IR spectra and no anhydride could be precipitated from the reaction mixture indicating no reaction had taken place.

COMPARATIVE EXAMPLE B

The reaction procedure described in Example 2 was repeated except the zinc chloride was eliminated and the reaction was maintained at 200° C. for sixteen hours. After the reaction cooled the total yield of ortho-sulfobenzoic acid anhydride was only 50% of the theoretical amount.

The comparative examples clearly demonstrate the improvement of the catalyzed reactions.

While this invention has been described by a number of specific embodiments, it is obvious that other variations and modifications may be made without departing from the spirit and scope of the invention as set forth in the appended claims.

The invention claimed is:

1. A process for the synthetic of ortho-sulfobenzoic acid anhydride which comprises heating a 2-sulfohalide benzoate in the presence of a catalytic amount of a Friedel-Crafts catalyst.

2. The process of claim 1 further characterized in that the 2-sulfohalide benzoate has the structure:

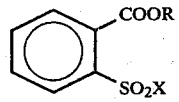

wherein R is aliphatic of 1 to about 12 carbons; aryl of 6 to about 18 carbons, or aralkyl of 7 to about 20 carbons and X is Cl or Br.

3. The process of claim 1 further characterized in that the 2-sulfohalide benzoate is heated in the presence of the Friedel-Crafts catalyst at a temperature ranging from about 130° C. to about 400° C.

4. The process of claim 3 further characterized in that the temperature ranges from about 150° C. to about 250° C.

5. The process of claim 1 further characterized in that the Friedel-Crafts catalyst is present at a level of at least about 0.01 percent by weight of the 2-sulfohalide benzoate.

6. The process of claim 5 further characterized in that the Friedel-Crafts catalyst is present at a level of between 0.1 to about 3.0 percent by weight of the 2-sulfohalide benzoate.

7. The process of claim 1 further characterized in that the catalyst is selected from the group of halides consisting of antimony, molybdenum, iron, boron, tin, zinc and titanium halides.

8. The process of claim 1 further characterized in that the catalyst is selected from the group of halides consisting of zinc chloride, and ferric chloride.

9. The process of claim 1 further characterized in that the 2-sulfohalide benzoate is heated in the absence of a solvent.

10. The process of claim 1 further characterized in that the 2-sulfohalide benzoate is heated in the presence of a solvent which is essentially inert to the conditions of the reaction.

11. The process of claim 10 further characterized in that the solvent has a boiling point of at least about 130° C.

12. The process of claim 11 further characterized in that the solvent has a boiling point of at least about 150° C.

13. A process for the synthetic of ortho-sulfobenzoic acid anhydride which comprises heating o-carbomethoxybenzenesulfonyl chloride in the presence of a catalytic amount of a Friedel-Crafts catalyst.

14. The process of claim 13 further characterized in that the o-carbomethoxybenzenesulfonyl chloride is heated in the presence of the Friedel-Crafts catalyst at a temperature ranging from about 130° C. to about 400° C.

15. The process of claim 14 further characterized in that the temperature ranges from about 150° C. to about 250° C.

16. The process of claim 13 further characterized in that the Friedel-Crafts catalyst is present at a level of at least about 0.01 percent by weight of the o-carbomethoxybenzenesulfonyl chloride.

17. The process of claim 13 further characterized in that the catalyst is selected from the group of halides consisting of antimony, molybdenum, iron, boron, tin, zinc and titanium halides.

18. The process of claim 13 further characterized in that the catalyst is selected from the group of halides consisting of zinc chloride, and ferric chloride.

19. The process of claim 16 further characterized in that the Friedel-Crafts catalyst is present at a level of between 0.1 to about 3.0 percent by weight of the o-carbomethoxybenzenesulfonyl chloride.

20. The process of claim 13 further characterized in that the o-carbomethoxybenzenesulfonyl chloride is heated in the absence of a solvent.

21. The process of claim 13 further characterized in that the o-carbomethoxybenzenesulfonyl chloride is heated in the presence of an inert solvent.

22. The process of claim 21 further characterized in that the solvent has a boiling point of at least about 130° C.

23. The process of claim 22 further characterized in that the solvent has a boiling point of at least about 150° C.

24. A process for the synthesis of ortho-sulfobenzoic acid anhydride which comprises heating at a temperature between about 130° C. and 400° C. o-carbomethoxybenzenesulfonyl chloride in the presence of 0.01 to about 3.0 percent based on the weight of the o-carbomethoxybenzenesulfonyl of a Friedel-Crafts catalyst.

25. The process of claim 24 further characterized in that the catalyst is selected from the group consisting of ferric chloride and zinc chloride.

* * * * *

UNITED STATES PATENT AND TRADEMARK OFFICE
CERTIFICATE OF CORRECTION

PATENT NO. : 4,408,058

DATED : October 4, 1983

INVENTOR(S) : MARK L. MITCHELL, III & RICHARD P. CARR

It is certified that error appears in the above-identified patent and that said Letters Patent are hereby corrected as shown below:

In the claims, column 4, line 49, "synthetic" should read --synthesis--.

Column 5, line 33, "synthetic" should read --synthesis--.

Signed and Sealed this

Thirteenth Day of December 1983

[SEAL]

Attest:

GERALD J. MOSSINGHOFF

Attesting Officer

Commissioner of Patents and Trademarks